United States Patent [19]
Wang

[11] Patent Number: 5,389,314
[45] Date of Patent: Feb. 14, 1995

[54] MEDICATION DISPENSING BALLOON CATHETER

[75] Inventor: James C. Wang, Norton, Mass.

[73] Assignee: Boston Scientific Corp., Del.

[21] Appl. No.: 88,327

[22] Filed: Jul. 7, 1993

Related U.S. Application Data

[62] Division of Ser. No. 862,415, Apr. 2, 1992, Pat. No. 5,254,089.

[51] Int. Cl.$^6$ .............................. A61M 25/10
[52] U.S. Cl. ........................ 264/25; 264/573; 264/154; 264/156; 264/317; 425/131.1
[58] Field of Search ............... 264/173, 514, 573, 317, 264/154, 156, 25; 425/380, 467, 326.1, 131.1; 604/96

[56] References Cited

U.S. PATENT DOCUMENTS

| | | | |
|---|---|---|---|
| 3,767,759 | 10/1973 | Wichterle et al. | 264/317 |
| 3,862,868 | 1/1975 | Spillers | 156/244.14 |
| 4,138,457 | 2/1979 | Rudd et al. | 425/326.1 |
| 4,265,848 | 5/1981 | Rüsch | 264/173 |
| 4,308,192 | 12/1981 | Okada et al. | 425/326.1 |
| 4,330,497 | 5/1982 | Agdanowski | 264/173 |
| 4,952,357 | 8/1990 | Euteneuer | 264/317 |
| 5,071,425 | 12/1991 | Gifford, III et al. | 264/573 |
| 5,112,305 | 5/1992 | Barath et al. | 604/96 |
| 5,252,159 | 10/1993 | Arney | 264/573 |

Primary Examiner—Jeffery R. Thurlow

[57] ABSTRACT

An inflatable medical device for the delivery of medications to an organ in the body including a catheter having a plurality of lumens (13, 22, 28) disposed therein. The distal end of the catheter is adapted to be disposed within a bodily organ. A hollow, inflatable, medication-deliverable balloon (16) is disposed on the distal end of the catheter and the interior of the balloon (16) is in fluid flow relationship with one of the lumens (22) to enable the balloon (16) to be inflated. An array of conduits (40) is disposed within the walls of the balloon for the delivery of medications to predetermined locations within said bodily organ. Another lumen (28) in the catheter shaft (14) is provided to deliver medications to the conduits (40) in the wall of the balloon (16). An egress (17) for the medications is provided so that they may be dispensed at the site being treated.

6 Claims, 2 Drawing Sheets

MEDICATION DISPENSING BALLOON CATHETER

This is a divisional of copending application Ser. No. 07/862,415 filed on Apr. 2, 1992, now U.S. Pat. No. 5,254,089.

BACKGROUND OF THE INVENTION

The present invention relates to a balloon that can dispense medications in a predetermined location within a bodily organ and especially relates to a balloon catheter which can simultaneously provide forcible expansion of the cross section of a coronary artery that has been narrowed by atherosclerotic lesion or stenosis and also dispense a medication to the site that has been forcibly expanded. In particular, the medication dispensing balloon of the present invention is disposed at the distal end of a catheter shaft having a plurality of lumens therein. The balloon not only forcibly expands the cross section of the coronary artery but also can simultaneously deliver a dosage of medication at the site of the expansion thereby to avoid injecting large quantities of the medications intravenously when only a small site needs to be treated. Moreover, the present invention relates to a inflatable medical device in which the wall of the balloon serves both as the containment mechanism for the inflation fluid and also as the dispensing vehicle for medications.

DESCRIPTION OF THE PRIOR ART

Balloon catheters for expanding atherosclerotic lesions or stenosises are well known in the art. Such devices include an inflatable balloon disposed at the end of a multi-lumen catheter shaft in which a pressurizing fluid is forced into the balloon to expand it and the expansion of the balloon engages the surface of the artery to enlarge its cross section. Such balloons, however, have not provided a means to dispense medications at the site of the lesion or stenosis but rather have relied upon either injecting massive doses of drugs intravenously or withdrawal of the balloon catheter and reinsertion of another catheter into the patient's arterial system to administer the medication.

The U.S. Pat. No. 5,049,132 to Shaffer et al describes a doubled walled balloon catheter in which one balloon is inflated to enlarge the artery and a circumferentially disposed second balloon is filled with a medication. The inside balloon is aperture-free and is mounted on a catheter shaft and receives inflation media from an inflation lumen in the catheter shaft. A second lumen is spaced from the first lumen and is carried by the catheter shaft also. A second balloon as mounted on the catheter shaft in communication with the second lumen and a large number of tiny apertures are formed in it. Upon application of significant pressure, the medications will flow through the apertures thereby providing for the administration of controlled quantities of medication. As is apparent, the construction of double walled balloons and mounting them on a catheter shaft is difficult and time consuming. Other examples of double walled balloon catheters for the administration of medications are disclosed in the United States patent to Shockey et al, U.S. Pat. No. 4,994,033 which also provides an outermost sleeve with a pattern of holes that are precisely controlled in their sizes.

In the United States patent to Buras, U.S. Pat. No. 4,693,243, a flexible non-collapsible conduit system is disclosed that is separably positioned about a cuffed endotracheal tube to allow for direct topical application of medicinal substances to tissues of the larynx which may be irritated by the endotracheal tube. An external injection port and tubing connect to the internal passage of the endotracheal shaft to enable the topical application of the medications while the shaft is in place within the larynx or trachea.

SUMMARY OF THE INVENTION

According to the present invention I have discovered an inflatable medical device for delivery of medications to an organ in the body in which a multi-luminal catheter shaft is disposed within a bodily organ, usual one of the arteries. An inflatable balloon is disposed at the end of the catheter shaft. The balloon is hollow and is medication-deliverable by means of an array of conduits disposed within the wall of the balloon. A medication-deliverable lumen within the catheter shaft is connected to the array of conduits by means of a manifold thereby to enable the balloon to dispense medications directly on the site of the stenosis or lesion through apertures in the walls of the conduit or at the distal ends of the conduits. The conduits preferably are radially arranged within the wall of the balloon and are individually segregated so they are not in fluid flow relationship with each other. With this radial arrangement and uniformly sized apertures, the medications can be dispensed evenly upon the diseased site being treated.

Quite importantly, the balloon of the present invention enables the physician to control the rate of release of medications as desired, independently of the inflation pressure of the balloon. If the inflation media for the balloon is the medication to be dispensed, and if a single balloon is used, the release rate of the medication is thus dependent upon the inflation pressure of the balloon. Lower pressures result in incomplete dilation and too high a pressure results in excessive drug release and even dissection of the organ in which it is disposed due to the production of "water jets". With the balloon of the present invention, there is only a minimal increase in the profile of the balloon resulting from the presence of the conduits. Since multiple channels exist in the balloon, it is possible to deliver more than one kind of drug without prior mixing and even simultaneous administration of the medications. Also, since the balloons have a plurality of conduits, some of the conduits can be used as heaters with the use electric wires or some can provide heated fluids. The use of a multiply conduited balloon is highly advantageous in that the walls of the balloon are integrally constructed with the conduits and thus there are no sealing surfaces to break nor welds to fail. The dispensing of medication is limited to predetermined locations thereby reducing the amount of medication necessary and therefore reducing side effects through the use of large amounts of drugs.

In the manufacture of the balloon, a hollow tube of two or more dissimilar plastics material is co-extruded using conventional extrusion techniques. A discrete phase, that is the phase which serves as the precursor of the conduits and which dictates their location and shape, is formed of high density polyethylene, Nylon, low density polyethylene or polyethylene copolymers. A continuous phase, that is the phase that will form the balloon with the discrete phase disposed therein, can be formed of polyethylene terapthalate or high density polyethylene. High density polyethylene, low density polyethylene and polyethylene copolymers can be extruded within polyethylene terapthalate and Nylon can be extruded within high density polyethylene. After the phases are co-extruded, the discrete phase is withdrawn from the continuous phase to leave the conduits inside the continuous phase. Co-extrusion of two plastics materials is well known and conventional techniques are used for such processes. The essential criteria for matching of the two plastics materials is that they not adhere to each other after extrusion and that the discrete phase can be withdrawn from the continuous phase and leave conduits in the continuous phase.

While co-extrusion is preferred to form the balloons, it is also possible to extrude tubes with the conduits already in them using known extrusion dies. Because the precursors to the conduits are so narrow, normally between about 0.025 and 1.75 mm. within a tube having a wall thickness between about 0.1 and 2.5 mm. and outside diameter between about 0.25 and 6.25 mm., I have found that extrusion with preformed conduits is not always satisfactory and that co-extrusion is best.

Following the extrusion of the conduited tube and the withdrawal of the discrete phase, the medication dispensing balloon of the present invention can be formed by heating the tube to a predetermined temperature in a predetermined location (which determines the length of the balloon) while applying pressure to the interior of the tube. The tube will inflate to form the balloon with the conduits formed within the walls of the balloon. After the balloon has been formed it can be attached to a multiluminal catheter shaft and then folded for use.

The many other objects, features and advantages of the present invention will become apparent from the following description.

BRIEF DESCRIPTION OF THE DRAWINGS

FIGS. 2B, 2D, 2F and 2H are exploded fragmentary views of the embodiments shown in FIGS. 2A, 2C, 2E and 2G respectively.

DESCRIPTION OF THE SPECIFIC EMBODIMENTS

Figure 1:
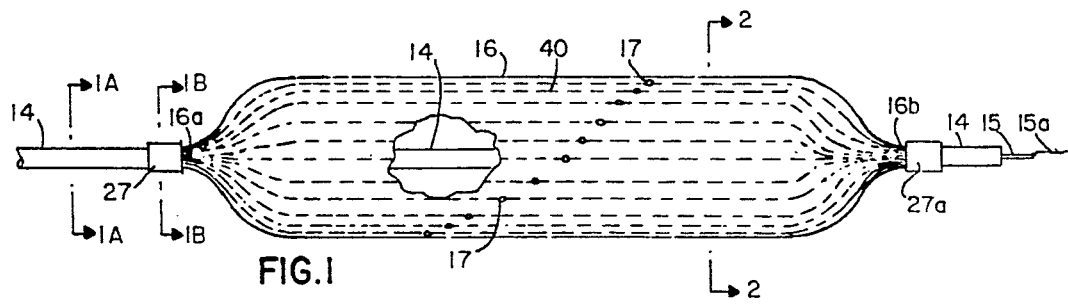
FIG. 1 is a side elevational view of a conduited medical balloon according the present invention. In this view the balloon is inflated and a portion of the balloon is cut away to show the interior of the balloon.
Figure 1A:
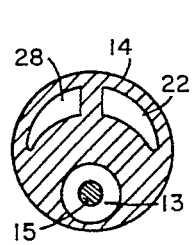
FIGS. 1A and 1B are cross-sectional views taken along the lines 1A—1A and 1B—1B respectively showing the lumens of the catheter shaft and the attachment between the catheter shaft and the balloon.
Figure 1B:
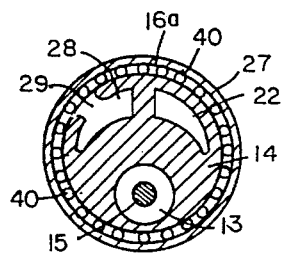

Referring to the drawings, a balloon-type catheter is shown. The balloon-type catheter of the present invention is similar to other catheters used for treating coronary artery disease except as otherwise shown and described. As is conventional, the catheter is attached to an array of hubs (not shown) being typically made of rigid materials. These hubs are utilized for the introduction of inflation fluids, medications and the disposition of a guide wire as will be described hereinafter. The hubs are attached to the proximal end of a multi-luminal tubing 14, as is conventional.

A medical balloon 16 is positioned at the distal end of the catheter shaft 14. Medical balloon 16 is made of the materials described herein and is heat sealed or adhesively attached (as is conventional) at its respective ends 16a and 16b to catheter shaft 14. A collar 27a is fitted around the distal end 16b of the balloon 16 and affixed thereto to hold the balloon 16 in place on the shaft 14. An inflation port 20 is formed in an inflation lumen 22 (shown in FIGS. 2A–2H). The port 20 provides communication between the interior of the balloon 16 and the inflation lumen 22. Lumen 22 also communicates with any desired source of compressed inflation fluid at the hub mentioned above as is conventional for balloon catheters.

A medication lumen 28 is provided within catheter shaft 14. Lumen 28 extends completely through the catheter and communicates with a medication injection port 29 at the proximal end of the catheter shaft 14. Aperture 29 is disposed within a manifold 27 (that is attached to both the balloon 16 and the shaft 14) and is in fluid flow communication with medication dispensing conduits 40 disposed within the balloon as will be described hereinafter.

A third lumen 13 extends completely through the catheter shaft 14 so that a conventional guidewire 15 with a conventional exploratory tip 15a may be inserted in balloon 13 to assist in catheter insertion in a conventional manner.

As mentioned previously lumen 28 is in fluid flow communication with an opening 29 that is disposed within manifold 27. Manifold 27 is in fluid flow communication with an array of conduits 40 disposed within the wall of balloon 16. In the preferred embodiments these conduits are radially arranged within the perimeter of wall 16, as best shown in FIGS. 2A–2H.

In the embodiment shown in FIG. 1, each of the conduits 40 is provided with an aperture 17 for the introduction of medication into the bodily organ that has been catheterized. While the Figure shows a helical array of apertures 17, any configuration that enables the introduction of medications can be used. The apertures 17 are easily formed in the conduits 40 by inflating both the balloon 16 and the conduits 40 with air and then pricking each conduit wall lightly with a pin until it is deflated or the conduits 40 can be pierced with laser irradiation. The apertures 17 preferably have openings of predetermined sizes in the range of 0.0025 to 2.5 mm. depending upon the viscosity of the medication being dispensed and the desired flow rate. On the other hand elongated slits on the outside of the conduit can be used also, if required. The preferred shape of the apertures is round, but oval, square and rectangular shapes have applicability.

Figure 2A:
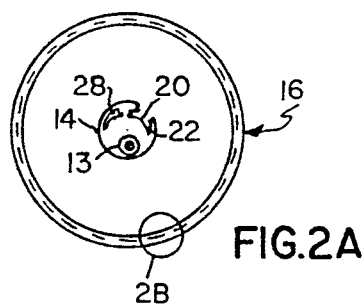
FIGS. 2A to 2H are cross-sectional views taken along the lines 2—2 of FIG. 1 and show various embodiments of the conduiting within the wall of the balloon.
Figure 2C:
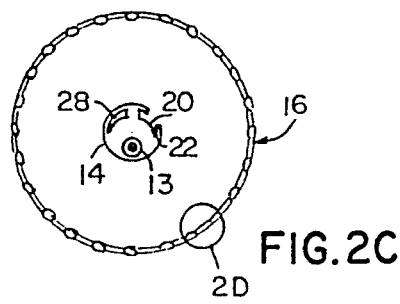
Figure 2B:
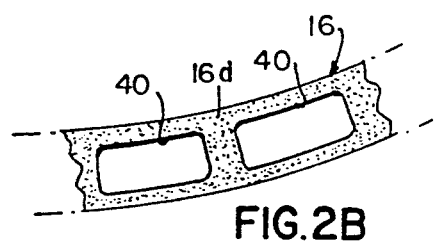
Figure 2D:
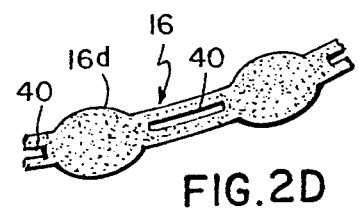

Variously shaped conduits 40 can be made, as depicted in FIGS. 2A to 2H. In FIGS. 2A and 2B a balloon 16 is shown having a uniform wall thickness with generally rectangular conduits 40 formed therein. The conduits 40 will contain the medication to be dispensed in the bodily organ being treated. The wall thickness of the balloon 16 can be between about 0.005 and 0.25 mm. with the conduits 40 each having a width and height between about 0.075 and 6.25 mm. The wall thickness between the conduits 40 and the wall thickness between the conduit 40 and the exterior of the balloon 16 can be between about 0.0025 and 0.125 mm.

In the embodiment shown in FIG. 2C, the conduit 40, as depicted, is merely a slit before being inflated with a medication. When the conduit 40 is filled with medication it can be enlarged significantly from inflation. The conduits can be spaced from each other by ribs 16d and the wall thicknesses can be similar.

Figure 2E:
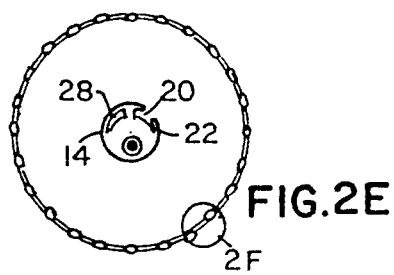
Figure 2G:
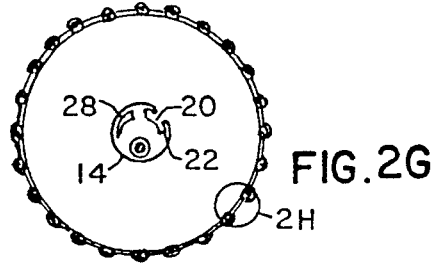
Figure 2F:
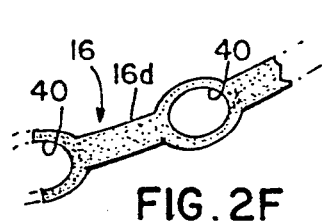
Figure 2H:
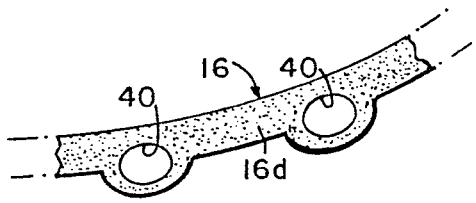

In FIGS. 2E and 2F another embodiment is shown in which the conduits 40 have a generally ovoid shape with the ribs 16d having a lesser width than the width of the conduits 40. In FIGS. 2G and 2H the conduits 40 again have a ovoid shape with the internal wall of the balloon 16 having a generally cylindrical shape and the exterior wall being formed with the ribs 16d spacing them apart.

In each of the embodiments shown in FIGS. 2A to 2H, the catheter shaft 14 extends entirely through the length of the balloon 16. The lumen 13 has the guidewire 15 and lumen 28 is used for the introduction of medications. An opening 20 is formed in lumen 22 to introduce expansion fluids into the balloon 20 to enable the balloon to be inflated at the site of the surgical treatment.

Figure 3A:
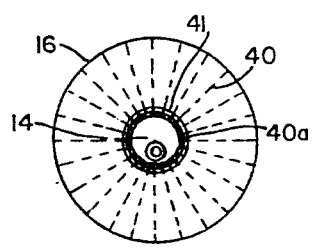
FIG. 3A is an end elevational view, partially in cross section, taken along the lines of 3A—3A of FIG. 3B.
Figure 3B:
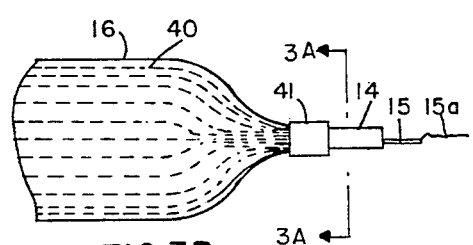
FIG. 3B is a side elevational view of another embodiment of the present invention for delivering medications to predetermined locations.

In FIG. 3A a balloon similar to that of FIG. 1 is shown. The medication, however, rather than be introduced through apertures 41 disposed within the balloon 16 are introduced through directly from the ends of the conduits 40. The distal end of the balloon 16 is attached to the catheter shaft 14 and the ends 40a of the conduits 40 empty directly from them. A ring 41 can be fitted around and attached to the distal end of the balloon 16 to aid in the construction.

It is apparent that modifications and changes can be made within the spirit and scope of the present invention but it is my intention, however, only to be limited by the scope of the appended claims.

As my invention I claim:

1. A method of making a medication dispensing balloon for a catheter, said method comprising:
   co-extruding two dissimilar plastic materials, the first of the extrusions forming a tube having a wall disposed about an axis and the other of said plastics being disposed within the wall of said tube, said other plastic being arranged as a segmented array of circumferentially disposed strands, said array being aligned parallel with said axis, said strands being individually enclosed within said tube;
   withdrawing said strands from said tube whereby to form a plurality of conduits within said tube.

2. The method according to claim 1 wherein the plastic forming said tube is high density polyethylene, low density polyethylene or polyethylene copolymers with the strands being polyethylene terephthalate or Nylon tubing with the strands being high density polyethylene.

3. The method according to claim 1 wherein the wall thickness of the extruded tube is between 0.05 and 3.75 mm. and the diameter of the strands is between about 0.0125 and 2.5 mm.

4. The method according to claim 1 further including the step of disposing dispensing means on the outer surfaces of each of said conduits.

5. The method according to claim 4 wherein said dispensing means are perforations on said conduits.

6. The method according to claim 4 wherein said conduits are imperforate over their lengths and terminate in apertures disposed at distal ends thereof whereby to provide egress for medications from said balloon.

* * * * *